(12) United States Patent
Yaegashi et al.

(10) Patent No.: US 6,946,566 B2
(45) Date of Patent: Sep. 20, 2005

(54) PROCESS FOR PREPARATION OF OPTICALLY ACTIVE HALOGENO HYDROXYPROPYL COMPOUND AND GLYCIDYL COMPOUND

(75) Inventors: Keisuke Yaegashi, Osaka (JP); Yoshiro Furukawa, Osaka (JP)

(73) Assignee: Daiso Co., Ltd., Osaka-Fu (JP)

( * ) Notice: Subject to any disclaimer, the term of this patent is extended or adjusted under 35 U.S.C. 154(b) by 5 days.

(21) Appl. No.: 10/629,776

(22) Filed: Jul. 30, 2003

(65) Prior Publication Data

US 2004/0024254 A1 Feb. 5, 2004

(30) Foreign Application Priority Data

Jul. 31, 2002 (JP) ........................... 2002-223293

(51) Int. Cl.[7] ........................... C07D 39/28; C07C 41/03
(52) U.S. Cl. ....................... 549/521; 568/674; 568/811; 568/844; 560/105; 560/111; 560/236
(58) Field of Search .................... 549/521; 568/674, 568/811, 844; 560/105, 111, 236

(56) References Cited

U.S. PATENT DOCUMENTS

2003/0088114 A1    5/2003   Larrow et al.

FOREIGN PATENT DOCUMENTS

| GB | 1 458 392 | 12/1976 |
| JP | 6-374823 | 5/1994 |
| JP | 2000-103788 | 4/2000 |
| WO | 00/09463 | 2/2000 |

OTHER PUBLICATIONS

Takano et al., "Practical Preparation of Optically Active O–O Benzylglycidol From Optically Active Epichlorohydrin", Heterocycles, vol. 31, No. 9, pp. 1715–1719 (1990).
Schaus et al., "Highly Selective Hydrolytic Kinetic Resolution of Terminal Epoxides Catalyzed by Chiral salen)Co[III] Complexes. Practical Synthesis of Enantioenriched Terminal Epoxides and 1,2–Diols", J. Am. Chem. Soc., vol. 124, No. 7 pp. 1307–1315 (2002).
Chemical Abstracts, vol. 114, No. 19, May 13, 1991, Columbus, Ohio, U.S.; abstract No. 185001, Takano Seiichi et al: "Preparation of optically–active 2–hydroxy–3–hydrocarbyloxypropyl halides or sulfonates", XP002257262 & JP 02 286643 A (Daiso Co., Ltd., Japan), Nov. 26, 1990.

Primary Examiner—Bernard Dentz
(74) Attorney, Agent, or Firm—Wenderoth, Lind & Ponack, L.L.P.

(57) ABSTRACT

A process for preparing regioselectively an optically active 1-halogeno-2-hydroxypropyl compound of the following formula;

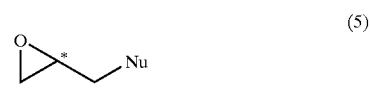

(4)

wherein X is halogen atom and Nu is a heteroatom having a substituent,
and an optically active glycidyl compound of the formula;

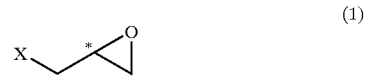

(5)

which comprises reacting an optically active epihalohydrin of the formula;

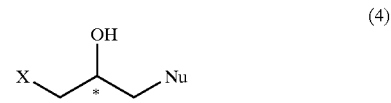

(1)

with a neucleophilic agent,
in the presence of a metal complex of the formula;

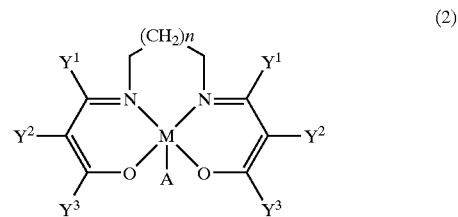

(2)

wherein n is an integer of 0, 1 or 2, $Y^1$, $Y^2$ and $Y^3$ are hydrogen atom, etc., and $Y^2$ and $Y^3$ may form a ring such as benzene, A is a counterion and M is a metal ion, and further subjecting the compound (4) to reaction with a base to prepare the optically active glycidyl compound (5).

29 Claims, No Drawings

PROCESS FOR PREPARATION OF OPTICALLY ACTIVE HALOGENO HYDROXYPROPYL COMPOUND AND GLYCIDYL COMPOUND

BACKGROUND OF THE INVENTION

The present invention relates to a novel process for preparation of an optically active 1-halogeno-2-hydroxypropyl compound and an optically active glycidyl compound useful as an intermediate for synthesis of medicines or agrochemicals.

The preparation methods for a glycidyl compound via a 1-halogeno-2-hydroxypropyl compound were reported in many documents from of old.

However, most of the methods relate to a process for preparation of a racemic glycidyl compound starting from a racemic epihalohydrin. The preparation methods for an optically active gycidyl compound starting from an optically active epihalohydrin were not reported in plenty. One of the reasons is because there is no significant difference in activity between the active positions on epihalohydrin, namely halogenomethylene at position 1 and the terminal position on epoxy ring at position 3 and therefore, it is not easy to handle it. Namely, as shown in the following reaction scheme, in reaction with a nucleophilic substance, it is considered that nucleophilic reaction shown by route a theoretically precedes to give a compound [I] or [II], but practically, thus specificity or selectivity is not complete and therefore, the reaction shown by route b also occurs to give a compound [III] in small amount as a side product. As a result, optical purity of the object compound [II] decreases.

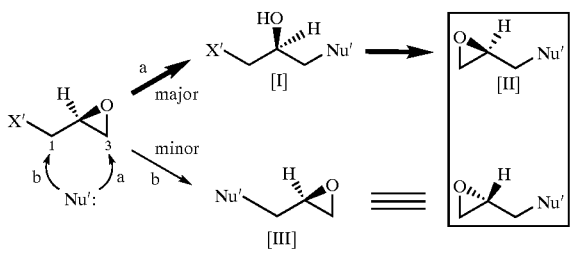

wherein X' is halogen atom and Nu' is a residue of nucleophilic substance.

In order to solve the above problem, several methods were developed, such as (i) a method for reacting an optically active epihalohydrin and 4-carbamoylmethylphenol in the presence of an alkali hydroxide and a quaternary ammonium salt in an aqueous solvent (Japanese Patent Publication B 6-374823, and (ii) a method for reacting an optically active epihalohydrin and benzylalcohol in the presence of boron trifluoride-diethyl ether (Heterocycles, 31, 1715 (1990)), but in any case, optical purity of the glycidyl compound obtained is 1–2% lower comparing with one of the epihalohydrin used for a starting material. Therefore, the improvement of the process of preparation for an optically active glycidyl compound is still desired.

On the other hand, according to a method for treating with potassium carbonate after the reaction with an optically active epichlorohydrin and water in the presence of an optically active cobalt (III) complex (J. Am. Chem. Soc. 124, 1307 (2002)), an optically active glycidol is obtainable in highly optical purity. However, in case of carrying out this reaction, an optically active cobalt (III) having a specific steric configuration have to be made and to be used according to each configuration of the epihalohydrin used as a starting material. Therefore, this method is troublesome and not economical.

DETAILED DESCRIPTION OF THE PREFERRED EMBODIMENTS

The present inventors have extensively studied to solve the above problems, too and as a result have found that by using a non-chiral metal complex shown in the formula (2) mentioned below as catalyst, an optically active 1-halogeno-2-hydroxypropyl compound and an optically active glycidyl compound are prepared in high yield and high purity. Thus the present invention has been completed.

Namely, the present invention relates to a process for preparing regioselectively an optically active 1-halogeno-2-hydroxypropyl compound of the following formula;

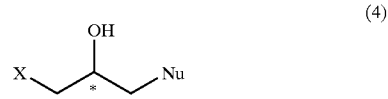

(4)

wherein X is halogen atom and Nu is a heteroatom having a substituent, and an optically active glycidyl compound of the formula;

(5)

wherein Nu is the same as define the above, which comprises reacting an optically active epihalohydrin of the formula;

(1)

wherein X is halogen,
with a nucleophilic agent of the formula;

Nu—Q (3)

wherein Q is hydrogen atom or silicon having a substituent and Nu is the same as defined above,
in the presence of a metal complex of the formula;

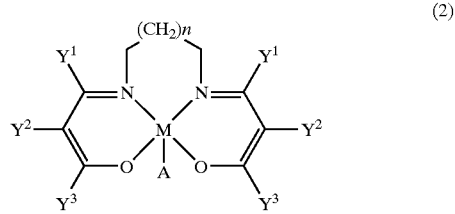

(2)

wherein n is an integer of 0, 1 or 2, $Y^1$, $Y^2$ and $Y^3$ are the same or different, hydrogen atom, halogen atom, intro group, alkyl group optionally substituted, aryl group optionally substituted, acyl group, or alkoxycarbonyl group, and $Y^1$ and $Y^2$, or $Y^2$ and $Y^3$, taken together with the carbon atoms to which they are attached, may form a ring, A is a counterion and M is a metal ion,
and further subjecting the compound (4) to reaction with a base to prepare the optically active glycidyl compound (5).

The present invention is explained in more detail as follows.

First the step to prepare an optically active 1-halogeno-2-hydroxypropyl compound (4) by reacting an optically active epihalohydrin (1) with a nucleophilic agent (3) in the presence of a metal complex (2) as catalyst is explained.

An optically active epihalohydrin shown by the formula (1) wherein X is chlorine atom or bromine atom is preferably used.

A metal complex shown by the formula (2) wherein $Y^1$ is hydrogen atom, and $Y^2$ and $Y^3$ taken together with the carbon atoms to which they are attached, form a ring such as benzene or cyclohexene ring optionally substituted, is preferably used.

Especially preferable metal complexes (2) are shown by the following formula (6):

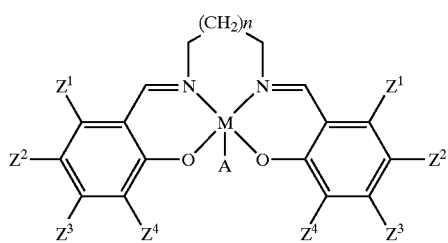

(6)

wherein n is an integer of 0, 1 or 2, $Z^1$, $Z^2$, $Z^3$ and $Z^4$ are the same or different, hydrogen atom, halogen atom, nitro group, straight alkyl group optionally substituted, aralkyl optionally substituted, aryl group optionally substituted, alkyloxy optionally substituted, aralkyloxy optionally substituted or aryloxy optionally substituted, or $Z^1$ and $Z^2$, $Z^2$ and $Z^3$, or $Z^3$ and $Z^4$, taken together with the carbon atoms to which they are attached, may form a ring, A is a counterion and M is a metal ion.

In the formula (6), $Z^1$, $Z^2$, $Z^3$ and $Z^4$ are, for example hydrogen atom, halogen atom, such as fluorine atom, chlorine atom, bromine atom or iodine atom, nitro group, straight or branched $C_{1-6}$ alkyl group, such as methyl, ethyl, n-propyl, isopropyl, 2,2-dimethylpropyl, n-butyl, sec-butyl, tert-butyl, n-heptyl or n-hexyl, $C_{3-7}$ cyclic alkyl group, such as cyclopentyl or cyclohexyl, substituted alkyl group such as trifluoromethyl or perfluoro-tert-butyl, aralkyl group optionally substituted, such as benzyl, 4-metylbenzyl or cumenyl, aryl group optionally substituted, such as phenyl, 4-methylphenyl, 1-naphthyl or 2-naphthyl, alkyloxy group optionally substituted, such as methoxy, ethoxy, tert-butoxy, trifluoromethoxy or perfluoro-tert-butoxy, aralkyloxy group optionally substituted, such as benzyloxy or 4-methylbenzyloxy, and aryloxy group optionally substituted, such as phenoxy or 4-methylphenoxy. $Z^1$ and $Z^2$, $Z^2$ and $Z^3$, or $Z^3$ and $Z^4$ are taken together with the carbon atoms to which they are attached, may form a ring, such as benzene ring or cyclohexene ring.

Preferably each of $Z^1$, $Z^2$, $Z^3$ and $Z^4$ is hydrogen, $Z^1$, $Z^2$ and $Z^3$ are hydrogen atom and $Z^4$ is tert-butyl, or $Z^1$ and $Z^3$ are hydrogen atom and $Z^2$ and $Z^4$ are tert-butyl.

Preferable one of embodiments of said metal complexes (2) or (6) is immobilized to an insoluble carrier, such as polymer, silica gel, alumina, zeolite and so on via ether bond or methylene bond.

As a counterion in the formula (2) or (6) for example, nitrate, halogen atom, such as fluoride, chloride or bromide, substituted alkoxide such as pentafluoro-tert-butoxide, substituted aryloxide such as pentafluorophenoxide or 2,4,6-trinitrophenoxide, alkylcarbonate optionally substituted, such as acetate, n-butyrate, trifluoroacetate or trichloroacetate, aralkylcarbonate optionally substituted, such as phenylacetate, 4-nitroacetate or 3,5-difluorophenylacetate, arylcarbonate optionally substituted, such as benzoate, pentafluorobenzoate or 2,4-dinitrobenzoate, alkylsulfonate optionally substituted, such as methanesulfonate, trifluoromethanesulfonate or (±)-comphorsulfonate, and arylsulfonate optionally substituted, such as benzenesulfonate, p-toluenesulfonate or 3-nitrobenzenesulfonate are illustrated. As preferable counterions, acetate, n-butyrate, (±)-comphorsulfonate, methanesulfonate, p-toluenesulfonate and trifluoromethanesulfonate are illustrated.

Metal ions shown by M in the formula (2) or (6) are not limited, but aluminum ion, titan ion, vanadium ion, chromium ion, manganese ion, iron ion, cobalt ion, nickel ion, molybdenum ion, ruthenium ion and tungsten ion are illustrated. Each metal ion corresponds to oxidized status of (II), (III) or (IV). Especially preferable ions are chromium ion (III) and cobalt ion (III).

For example, a cobalt (III) complex is easily prepared by subjecting a cobalt complex (II) of the following formula (8);

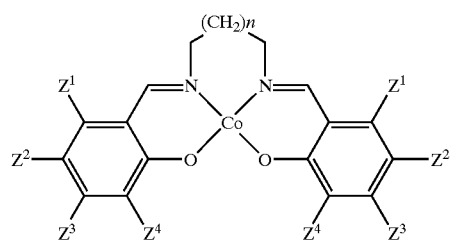

(8)

wherein n, $Z^1$, $Z^2$, $Z^3$ and $Z^4$ are the same as defined in the formula (6), to air oxidation in the presence of an acid which corresponds to a compound formed by binding a hydrogen atom to an electron-withdrawing substituent shown by A mentioned above in a solvent at room temperature.

The amount of the acid is 1–10 moles to cobalt (II) complex, preferably 1–2 moles. The cobalt complex (II) is easily prepared by a known method, namely by complex formation reaction consisting of admixing cobalt (II) acetate tetrahydrate and a salen ligand prepared by coupling alkyldiamine (1 mol) and salicylaldehyde (2 mol).

Other metal complexes used for the present invention are also easily prepared by a known method.

The amount of the metal complex is 0.1–10 mol % per optically active epihalohydrin, preferably 1–5 mol %. In regard to cobalt (III), the reaction solution itself after air oxidation of the cobalt (II) by the method mentioned above, may be served. Further, the reaction well proceeds by use of sole a metal complex as catalyst, but the reaction can be promoted by addition of a bulky tertial amine, such as N,N-diisopropylethylamine or triisobutylamine in the amount of 0.1 to 100 mole %.

The examples of substituents shown by Nu in a nucleophilic agent of the formula (3) are not limited as long as they are heteroatoms having a substituent, but for example ones having a substituent, such as alkyl optionally substituted, aralkyl optionally substituted, aryl optionally substituted, alkylcarbonyl optionally substituted, aralkylcarbonyl optionally substituted or arylcarbonyl optionally substituted, on heteroaroms, such as oxygen atom, sulfur atom, selenium atom, nitrogen atom, phosphorus atom or arsenic atom, are illustrated. Examples of substituents shown by Q are hydrogen atom, and straight or branched alkylsilyl group, such as trimethylsilyl, triethylsilyl or triisopropylsilyl.

Preferable nucleophilic agents (3) are shown by the following formula (7):

wherein R is hydrogen atom, straight, branched or cyclic alkyl group, straight, branched or cyclic alkylcarbonyl group, aralkyl group optionally substituted, aralkylcarbonyl group optionally substituted, aryl group optionally substituted or arylcarbonyl group optionally substituted.

Examples of substituents shown by R are hydrogen atom, straight, branched or cyclic alkyl, such as methyl, ethyl, isopropyl, cyclopentyl or cyclohexyl, aralkyl group optionally substituted, such as benzyl, 3-bromobenzyl or 4-methoxybenzyl, aryl group optionally substituted, such as phenyl, tolyl, 4-fluorophenyl or 2-allyloxyphenyl, alkylcarbonyl group optionally substituted, such as acetyl, propionyl, butyryl or pivaloyl, or aralkylcarbonyl group optionally substituted, such as phenylacetyl or 2-bromophenylacetyl, and arylcarbonyl group optionally substituted, such as benzoyl, 2,4,6-trimethylbenzoyl or 4-phenylbenzoyl.

The amount of the nucleophilic agent is 0.5–2.0 mole, preferably 0.8–1.2 mole to the optically active epihalohydrin (1).

The solvents used in the present reaction include ethers, such as, diethyl ether, 1,2-dimethoxyethane, tetrahydrofuran, tert-butylmethyl ether or cyclopentylmethyl ether, chlorinated compounds, such as chloroform, dichloromethane or 1,2-dichloroethne, hydrocarbons, such as hexane, heptane, benzene or toluene, esters, such as ethyl acetate or butyl acetate, ketones, such as acetone or 2-butanone, aprotic solvents, such as dimethlformamide, dimethyl sulfoxide or acetonitrile, and a mixture thereof, preferably ethers, such as tetrahydrofuran and tert-butylmethyl ether. The amount of these solvents is not limited. The reaction may be carried out without the solvent.

The reaction is carried out from −80° C. to refluxing temperature of the solvent, preferably −50° C. to 50° C., especially preferably 0° C. to 30° C. without the pressure or under the pressure.

After the reaction is completed, the reaction mixture can be served in the following reaction without further treatment.

After extraction, washing with water, or removal of excess solvent under reduced pressure, the residue is distilled, recrystalized or subjected to silica gel chromatography to give an optically active 1-halogeno-2-hydroxypropyl compound (4) with highly optical purity and activity.

Next, the step to prepare an optically active glycidyl compound by subjecting an optically active 1-halogeno-2-hydroxypropyl compound (4) obtained in the above mentioned step to cyclizing reaction in the presence of a base is explained as follows.

The bases include alkali or alkaline earth metal hydroxides, such as sodium hydroxide, potassium hydroxide or calcium hydroxide, alkali or alkaline earth metal carbonates, such as sodium carbonate, potassium carbonate, calcium carbonate or cesium carbonate, alkali metal alkoxide, such as sodium methoxide, sodium ethoxide, sodium benzyloxide, sodium phenoxide or potassium tert-butoxide, alkali metal, such as sodium or potassium, alkali metal hydride, such as sodium hydride or potassium hydride, alkali or alkaline earth metal amide, such as sodium amide or magnesium amide, and amines, such as 1,1,3,3-tetramethylguanidine, 1,5-diazabicyclo[4.3.0]none-5-ene or 1,8-diazabicyclo[5.4.0]-7-undecene. However in case of containing carbonyl group in Nu of the compound (4), the alkali or alkaline earth metal hydroxides mentioned above are not used because the compound (4) is hydrolyzed thereby.

The amount of the base is 1 mole or more, preferably 1.1 to 2.0 moles to the optically active 1-halogeno-2-hydroxypropyl compound.

In addition, the present reaction well proceeds using only the base, but the reaction is promoted by addition of 4-dimethylaminopyridine, a crown ether, such as 15-crawn-5 or 18-crown-6, an alkali metal iodide, such as sodium iodide or potassium iodide, or an alkali metal bromide, such as sodium bromide or potassium bromide 0.1 to 10 mole. %.

The solvents used in this reaction are classified into aqueous solvents and water-insoluble solvents. The formers include ethers, such as 1,2-dimethoxyethane, tetrahydrofuran or. 1,4-dioxane, aprotic solventa, such as dimethlformamide, dimethyl sulfoxide or acetonitrile, and a mixture thereof, and the latters include ethers, such as diethy ether, diisopropyl ether or tert-butylmethyl ether, chlorinated compounds, such as chloroform, dichloromethane or 1,2-dichloroethne, hydrocarbons, such as hexane, heptane, benzene or toluene, and a mixture thereof. The amount of these solvents is not limited.

The water-insoluble solvent can be used as two phase reaction with an aqueous solvent containing a base. However in case of containing carbonyl group in Nu of the compound (4), the compound is not used because the compound is hydrolyzed. The bases contained in the aqueous solvent include alkali or alkaline earth metal hydroxides, such as sodium hydroxide, potassium hydroxide or calcium hydroxide, and alkali or alkaline earth metal carbonates, such as sodium carbonate, potassium carbonate or calcium carbonate, preferably sodium hydroxide and potassium hydroxide. Furthermore, in case of the two phase reaction, the reaction is remarkably promoted by addition of phase transfer catalyst. The phase transfer catalyst includes quaternary ammonium salts, such as tetrabutylammonium chloride, tetrabutylammonium bromide, benzyltrimethylammonium bromide, benzyltriethylammonium chloride, benzyltributylammonium chloride, methyltrioctylammonium chloride, tetraoctylammonium bromide or N-benzylquininium chloride, quaternary phosphonium salts, such as tetrabutylphosphonium chloride, tetrabutylphosphonium bromide, tetraphenylphosphonium chloride, tetraphenylphosphonium bromide, benzyltriphenylphosphonium chloride or benzyltriphenylphosphonium bromide, and crown ethers, such as 12-crown-4, 15-crown-5 or 18-crown-6. The amount is 0.1 to 10 mole % to a substrate.

The reaction is carried out at −80 to 50° C. In case of use of the two phase solvent consisting of a water insoluble solvent and an aqueous solvent (water) containing a base, the reaction is preferably carried out at 0 to 50° C. for avoid of being freezed. The reaction is carried out at the pressure or without the pressure.

After the reaction, by subjecting to separating procedure by extraction, washing with water, removal of excess solvent under the reduced pressure, distillation of the residue, recrystalization or purification by silica gel chromatography, there is obtainable an optically active glycidyl compound (5) with highly optical purity and activity.

EXAMPLE

The present invention is illustratively explained by following examples, but is not limited by the examples.

In the examples, quantitative analysis by gas chromatography means quantitative determination of the product by gas chromatography using inner standard method (inner standard substance: m-dimethoxybenzene), and optical purity analysis by gas chromatography means optical purity measurement by optically active capillary column (G-TA/GL Science company) and optical purity analysis by HPLC (High performance liquid chromatography) means optical purity measurement by optically active column (CHIRALCEL OD-H/Daicel Company).

Example 1
Preparation of (S)-3-chloro-1,2-propanediol

To a mixture of N',N'-bis(3,5-di-tertbutylsalicylidene)ethylenediaminatocobalt(II) (119 mg, 0.216 mmol) and tetrahydrofuran (THF) (2.0 ml) was added (±) camphorsulfonic acid (60.3 mg, 0.260 mmol) and the reaction system was stirred for 1 hour while being filled with air. Thereto, namely to cobalt (III) complex in THF solution was added (S)-epichlorohydrin (1.00 g, 10.8 mmol, optical purity 99% e.e.) and water (234 µl, 13.0 mmol) in order, and the mixture was stirred for 20 hours at room temperature. After the reaction, quantitative analysis and optical purity measurement were conducted by gas chromatography on the reaction solution. As a result the subject compound, (S)-3-chloro-1,2-propanediol. (1.14 g, 95.4%) was produced with optical purity at 99% e.e.

Example 2
Preparation of (R)-3-chloro-1,2-propanediol

To a mixture of N',N'-bis(3,5-di-tertbutylsalicylidene)ethylenediaminatocobalt(II) (119 mg, 0.216 mmol) and tetrahydrofuran (THF) (2.0 ml) was added (±) camphorsulfonic acid (60.3 mg, 0.260 mmol) and the reaction system was stirred for 1 hour while being filled with air. Thereto, namely to cobalt (III) complex in THF solution was added (R)-epichlorohydrin (1.00 g, 10.8 mmol, optical purity 99% e.e.) and water (234 µl, 13.0 mmol) in order, and the mixture was stirred for 20 hours at room temperature. After the reaction, quantitative analysis and optical purity measurement were conducted by gas chromatography on the reaction solution. As a result the subject compound, (R)-3-chloro-1,2-propanediol (1.12 g, 93.7%) was produced with optical purity at 99% e.e.

Example 3
Preparation of (R)-glycidylphenyl Ether

To a mixture of N',N'-disalicylidene ethylenediaminatocobalt(II) (173 mg, 0.532 mmol) and dichloromethane (13 ml) was added (±) camphorsulfonic acid (148 mg, 0.638 mmol) and the reaction system was stirred for 1 hour while being filled with air. The reaction solution was evaporated to dryness under reduced pressure to give a crude blackish (dark) brown cobalt (III) complex. Thereto was added tert-butylmethyl ether (5 ml) to disperse the crude cobalt (III) complex and then thereto were added (S)-epichlorohydrin (2.50 ml, 31.9 mmol, optical purity 99% e.e.) and phenol (2.50 g, 26.6 mmol) in order. The mixture was stirred for 24 hours under nitrogen atmosphere at room temperature. After the reaction, the reaction mixture was diluted with tert-butylmethyl ether (20 ml), the solution was washed with a 6% aqueous sodium hydroxide solution (10 ml) and a saturated sodium chloride solution (10 ml) in order, and the organic layer was condensed under reduced pressure to give crude (S)-1-chloro-3-phenoxy-2-propanol (5.75 g). This crude compound (5.75 g) was dissolved in isopropanol (10 ml) and thereto was added a 24% aqueous sodium hydroxide solution (6.64 g, 39.8 mmol) under ice-cooling. The mixture was stirred for 1 hour at room temperature. After the reaction, the reaction mixture was diluted with tert-butylmethyl ether (50 ml) and the solution was washed with water (20 ml), a saturated aqueous ammonium solution (20 ml) and a saturated aqueous sodium chloride solution (20 mm) in order. The organic layer was condensed under reduced pressure to give (R)-glycidylphenyl ether (3.96 g). Quantitative analysis by gas chromatography and optical purity measurement by HLPC were conducted on the compound. As a result the subject compound, (R)-glycidylphenyl ether (3.80 g, 95.4%) was produced with optical purity at 99% e.e.

Example 4
Preparation of (S)-glycidylphenyl Ether

To a mixture of N',N'-disalicylidene ethylenediaminatocobalt(II) (173 mg, 0.532 mmol) and dichloromethane (13 ml) was added (±) camphorsulfonic acid (148 mg, 0.638 mmol) and the reaction system was stirred for 1 hour while being filled with air. The reaction solution was evaporated to dryness under reduced pressure to give a crude blackish (dark) brown cobalt (III) complex. Thereto was added tert-butylmethyl ether (5 ml) to disperse the crude cobalt (III) complex and then thereto were added (R)-epichlorohydrin (2.50 ml, 31.9 mmol, optical purity 99% e.e.) and phenol (2.50 g, 26.6 mmol) in order. The mixture was stirred for 24 hours under nitrogen atmosphere at room temperature. After the reaction, the reaction mixture was diluted with tert-butylmethyl ether (20 ml), the solution was washed with a 6% aqueous sodium hydroxide solution (10 ml) and a saturated sodium chloride solution (10 ml) in order, and the organic layer was condensed under reduced pressure to give crude (R)-1-chloro-3-phenoxy-2-propanol (5.44 g). This crude compound (5.44 g) was dissolved in isopropanol (10 ml) and thereto was added a 24% aqueous sodium hydroxide solution (6.64 g, 39.8 mmol) under ice-cooling. The mixture was stirred for 1 hour at room temperature. After the reaction, the reaction mixture was diluted with tert-butylmethyl ether (50 ml) and the solution was washed with water (2.0 ml), a saturated aqueous ammonium solution (20 ml) and a saturated aqueous sodium chloride solution (20 ml) in order. The organic layer was condensed under reduced pressure to give crude (S)-glycidylphenyl ether (3.80 g). Quantitative analysis by gas chromatography and optical purity measurement by HLPC were conducted on the compound. As a result the subject compound, (S)-glycidylphenyl ether (3.71 g, 93.0%) was produced with optical purity at 99% e.e.

Example 5
Preparation of (R)-glycidylphenyl Ether

To a mixture of N',N'-disalicylidene ethylenediaminatocobalt(II) (138 mg, 0.425 mmol) and dichloromethane (10 ml) was added methanesulfonic acid (3 µl, 0.510 mmol) and the reaction system was stirred for 1 hour while being filled with air. The reaction solution was evaporated to dryness under reduced pressure to give a crude blackish (dark) brown cobalt (III) complex. Thereto was added tert-butylmethyl ether (4 ml) to disperse the crude cobalt (III) complex and then thereto were added (S)-epichlorohydrin (2.00 ml, 25.5 mmol, optical purity 99% e.e.) and phenol (2.00 g, 21.3 mmol) in order. The mixture was stirred for 24 hours under nitrogen atmosphere at room temperature. After the reaction, the reaction mixture was diluted with tert-butylmethyl ether (20 ml), the solution was washed with a 6% aqueous sodium hydroxide solution (10 ml) and a saturated sodium chloride solution (10 ml) in order, and the organic layer was condensed under reduced pressure to give crude (S)-1-chloro-3-phenoxy-2-propanol (4.85 g). This crude compound (4.85 g) was dissolved in isopropanol (10 ml) and thereto was added a 24% aqueous sodium hydroxide solution (4.50 g, 25.5 mmol) under ice-cooling. The mixture was stirred for 1 hour at room temperature. After the reaction, the reaction mixture was diluted with tert-butylmethyl ether (50 ml) and the solution was washed with water (20 ml), a saturated aqueous ammonium solution (20 ml) and a saturated aqueous sodium chloride solution (20 ml) in order. The organic layer was condensed under reduced pressure to give crude (R)-glycidylphenyl ether (3.24 g). Quantitative analysis by gas chromatography and optical purity measurement by HLPC were conducted on the compound. As a result the subject compound, (R)-glycidylphenyl ether (3.07 g, 96.1%) was produced with optical purity at. 99% e.e.

Example 6
Preparation of (R)-glycidylemethyl ether

To a mixture of N',N'-disalicylidene ethylenediaminatocobalt(II) (70.2 mg, 0.216 mmol) and dichloromethane (5 ml) was added (±) camphorsulfonic acid (60.3 mg, 0.260 mmol) and the reaction system was stirred for 1 hour while being filled with air. The reaction solution was evaporated to dryness under reduced pressure to give a crude blackish (dark) brown cobalt (III) complex. Thereto was added tert-butylmethyl ether (2 ml) to disperse the crude cobalt (III) complex and then thereto were added (S)-epichlorohydrin (11.0 g, 10.8 mmol, optical purity 99% e.e.) and methanol (527 micro 1, 13.0 mmol) in order. The mixture was stirred for 72 hours under nitrogen atmosphere at room temperature. After the reaction, the reaction mixture was diluted with tert-butylmethyl ether (20 ml), the solution was washed with a 6% aqueous sodium hydroxide solution (10 ml) and a saturated sodium chloride solution (10 ml) in order, and the organic layer was condensed under reduced pressure to give crude (S)-chloro-3-methoxy-2-propanol (1.54 g). This crude compound (1.54 g) was dissolved in isopropanol (5 ml) and thereto was added a 24% aqueous sodium hydroxide solution (2.70 g, 16.2 mmol) under ice-cooling. The mixture was stirred for 1 hour at room temperature. After the reaction, the reaction mixture was diluted with tert-butylmethyl ether (20 ml) and the solution was washed with water (10 ml), a saturated aqueous ammonium solution (10 ml) and a saturated aqueous sodium chloride solution (10 ml) in order. The organic layer was condensed under reduced pressure to give crude (R)-glycidylphenyl ether (2.90 g). Quantitative analysis by gas chromatography and optical purity measurement by HLPC were conducted on the compound. As a result the subject compound, (R)-glycidylphenyl ether (0.763 g, yield 80.2%) was produced with optical purity at 99% e.e.

Example 7
Preparation of (R)-glycidylacetate

To a mixture of N',N'-disalicylidene ethylenediaminatocobalt(II) (70.2 mg, 0.216 mmol) and dichloromethane (5 ml) was added trifluoromethanesulfonic acid (23 µl, 0.260 mmol) and the reaction system was stirred for 1 hour while being filled with air. The reaction solution was evaporated to dryness under reduced pressure to give a crude blackish (dark) brown cobalt (III) complex. Thereto was added tert-butylmethyl ether (2.0 ml) to disperse the crude cobalt (III) complex and then thereto were added (S)-epichlorohydrin (1.0 g, 10.8 mmol, optical purity 99% e.e.) and acetic acid (742 µl, 13.0 mmol) in order. The mixture was stirred for 48 hours under nitrogen atmosphere at room temperature. After the reaction, the reaction mixture was diluted with tert-butylmethyl ether (8.0 ml) and to the solution was added potassium tertbutoxide (1.46 g, 13.0 mmol) under ice-cooling and the mixture was stirred for 1 hour. After the reaction, thereto was added ammonium chloride (116 mg, 2.16 mmol) and the mixture was stirred for 30 minutes. The precipitation was removed by filtration and the filtrate was condensed under reduced pressure to give crude (R)-glycidylacetate (1.38 g). Quantitative analysis and optical purity measurement by gas chromatography were conducted on the compound. As a result the subject compound, (R)-glycidylacetate (0.795 g, yield 63.4%) was produced with optical purity at 99% e.e.

Example 8
Preparation of (R)-glycidylacetate

To a mixture of N',N'-bis(3,5-di-tertbutylsalicylidene) ethylenediaminatocobalt(II) (119 mg, 0.216 mmol) and dichloromethane (5.0 ml) was added trifluoromethanesulfonic acid (23 µl, 0.260 mmol) and the reaction system was stirred for 1 hour while being filled with air. The reaction solution was evaporated to dryness under reduced pressure to give a crude blackish (dark) brown cobalt (III) complex. Thereto was added tertbutylmethyl ether (2.0 ml) to disperse the crude cobalt (III) complex and then thereto were added (S)-epichlorohydrin (11.0 g, 10.8 mmol, optical purity 99% e.e.) and acetic acid (742 µl, 13.0 mmol) in order. The mixture was stirred for 24 hours under nitrogen atmosphere at room temperature. After the reaction, the reaction mixture was diluted with tert-butylmethyl ether (8.0 ml) and to the solution was added potassium tert-butoxide (1.46 g, 13.0 mmol) under ice-cooling and the mixture was stirred for 1 hour. After the reaction, thereto was added ammonium chloride (116 mg, 2.16 mmol) and the mixture was stirred for 30 minutes. The precipitation was removed by filtration and the filtrate was condensed under reduced pressure to give crude (R)-glycidylacetate (1.36 g). Quantitative analysis and optical purity measurement by gas chromatography were conducted on the compound. As a result the subject compound, (R)-glycidylacetate (0.802 g, yield 63.9%) was produced with optical purity at 99% e.e.

Example 9
Preparation of (S)-3-chloro-1.2-propanediol 1-(n-butyrate)

A mixture of N',N'-bis(3,5-di-tert-butylsalicylidene) ethylenediaminatocobalt(II) (1.49 g, 2.70 mmol) and n-butyric acid (52.4 g, 0.594 mol) was stirred at 50 C for 1 hour while being filled with air. Thereto, namely to cobalt (III) complex in n-butyric acid solution were added N,N-diisopropylamine (6.89 g, 54.0 mmol) and (S)-epichlorohydrin (50.0 g, 0.540 mol, optical purity 99% e.e.) in order, and the mixture was stirred for 24 hours at room temperature. After the reaction, the reaction solution was distilled under reduced pressure to give the subject compound, (S)-3-chloro-1,2-propanediol 1-(n-butyrate) (80.0 g, yield 82.0%). The optical purity on the subject compound was 99% e.e. by measurement by HPLC.

Example 10
Preparation of (R)-glycidyl n-butyrate (S)-3-chloro-1,2-propanediol 1-(n-butyrate)(50.0 g, 0.277 mol, optical purity 99% e.e.) was dissolved in 1,2-dichloroethane (200 ml), followed by addition of potassium tert-butoxide (32.6 g, 0.291 mol) in ice-cooling. The mixture was stirred for 1 hour. After the reaction, the reaction mixture was added into a separating funnel, washed with water (200 ml) twice, the organic layer was condensed under reduced pressure to give the subject compound, (R)-glycidyl n-butyrate (28.7 g, yield 72.0%). The optical purity on the subject compound was 99% e.e. by measurement by HPLC.

According to the present invention, an optically active 1-halogeno-2-hydroxypropyl compound or an optically active glycidyl compound is prepared in good yield in the state that highly optical purity of a starting material, an optically active epihalohydrin is kept.

The present invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A process for preparing regioselectively an optically active 1-halogeno-2-hydroxypropyl compound of the following formula;

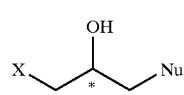
(4)

wherein X is halogen atom and Nu is a heteroatom having a substituent, which comprises reacting an optically active epihalohydrin of the formula;

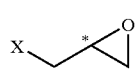
(1)

wherein X is halogen,
with a nucleophilic agent of the formula;

Nu—Q  (3)

wherein Q is hydrogen atom or silicon having a substituent and Nu is the same as defined above,
in the presence of a metal complex of the formula;

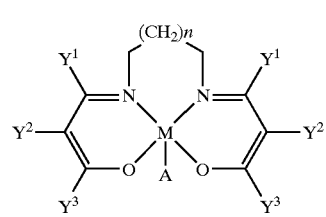
(2)

wherein n is an integer of 0, 1 or 2, $Y^1$, $Y^2$ and $Y^3$ are the same or different, hydrogen atom, halogen atom, nitro group, alkyl group optionally substituted, aryl group optionally substituted, acyl group, or alkoxycarbonyl group, and $Y^1$ and $Y^2$, or $Y^2$ and $Y^3$, taken together with the carbon atoms to which they are attached, may form a ring, A is a counterion and M is a metal ion.

2. A process for preparing an optically active glycidyl compound of the formula;

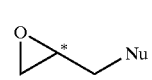
(5)

wherein Nu is a heteroatom having a substituent, which comprises reacting an optically active epihalohydrin of the formula;

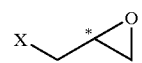
(1)

wherein X is halogen, with a nucleophilic agent of the formula;

Nu—Q  (3)

wherein Q is hydrogen atom or silicon having a substituent and Nu is the same as defined above, in the presence of a metal complex of the formula;

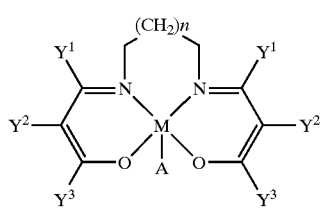
(2)

wherein n is an integer of 0, 1 or 2, $Y^1$, $Y^2$ and $Y^3$ are the same or different, hydrogen atom, halogen atom, nitro group, alkyl group optionally substituted, aryl group optionally substituted, acyl group, or alkoxycarbonyl group, and $Y^1$ and $Y^2$, or $Y^2$ and $Y^3$, taken together with the carbon atoms to which they are attached, may form a ring, A is a counterion and M is a metal ion, to prepare regioselectively an optically active 1-halogeno-2-hydroxypropyl compound of the following formula;

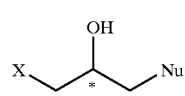
(4)

wherein X and Nu are the same as defined above, and further subjecting the compound (4) to reaction with a base.

3. The process of claim 1 wherein X in the formulae (1) and (4) is chlorine atom or bromine atom.

4. The process of claim 1 wherein the compound (2) is a compound of a following formula (6):

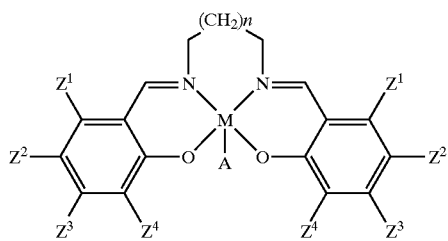

wherein n is an integer of 0, 1 or 2, $Z^1$, $Z^2$, $Z^3$ and $Z^4$ are the same or different, hydrogen atom, halogen atom, nitro group, straight alkyl group optionally substituted, aralkyl optionally substituted, aryl group optionally substituted, alkyloxy optionally substituted, aralkyloxy optionally substituted or aryloxy optionally substituted $Z^1$ and $Z^2$, $Z^2$ and $Z^3$, or $Z^3$ and $Z^4$, taken together with the carbon atoms to which they are attached, may form a ring, and A is a counterion and M is a metal ion.

5. The process of claim 1 wherein the neucleophilic agent (3) is a compound of a following formula (7):

R—OH wherein R is hydrogen atom, straight or branched alkyl group, straight or branched alkylcarbonyl group, aralkyl group optionally substituted, aralkylcarbonyl group optionally substituted, aryl group optionally substituted or arylcarbonyl group optionally substituted.

6. The process of claim 1 wherein M in the compound (2) is vanadium ion, chromium ion, manganese ion, iron ion, cobalt ion, nickel ion, molybdenum ion, ruthenium ion or tungsten ion.

7. The process of claim 1 wherein A in the compound (2) is acetate, n-butyrate, (±)-comphorsulfonate, methanesulfonate, p-toluenesulfonate or trifluoromethanesulfonate.

8. The process of claim 1 wherein the process for preparation for the compound (4) starting from the compound (1) is carried out in an ether as a reaction solvent.

9. The process of claim 2 wherein X in the formulae (1) and (4) is chlorine atom or bromine atom.

10. The process of claim 2 wherein the compound (2) is a compound of a following formula (6):

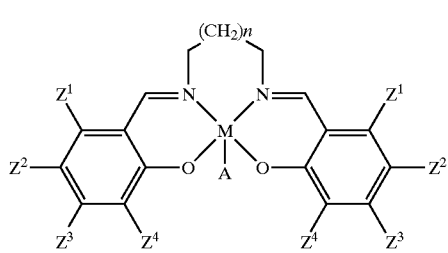

wherein n is an integer of 0, 1 or 2, $Z^1$, $Z^2$, $Z^3$ and $Z^4$ are the same or different, hydrogen atom, halogen atom, nitro group, straight alkyl group optionally substituted, aralkyl optionally substituted, aryl group optionally substituted, alkyloxy optionally substituted, aralkyloxy optionally substituted or aryloxy optionally substituted $Z^1$ and $Z^2$, $Z^2$ and $Z^3$, or $Z^3$ and $Z^4$, taken together with the carbon atoms to which they are attached, may form a ring, and A is a counterion and M is a metal ion.

11. The process of claim 3 wherein the compound (2) is a compound of a following formula (6):

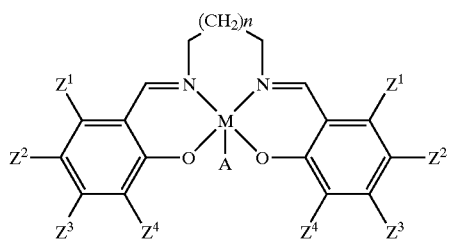

wherein n is an integer of 0, 1 or 2, $Z^1$, $Z^2$, $Z^3$ and $Z^4$ are the same or different, hydrogen atom, halogen atom, nitro group, straight alkyl group optionally substituted, aralkyl optionally substituted, aryl group optionally substituted, alkyloxy optionally substituted, aralkyloxy optionally substituted or aryloxy optionally substituted $Z^1$ and $Z^2$, $Z^2$ and $Z^3$, or $Z^3$ and $Z^4$, taken together with the carbon atoms to which they are attached, may form a ring, and A is a counterion and M is a metal ion.

12. The process of claim 2 wherein the nucleophilic agent (3) is a compound of a following formula (7):

R—OH wherein R is hydrogen atom, straight or branched alkyl group, straight or branched alkylcarbonyl group, aralkyl group optionally substituted, aralkylcarbonyl group optionally substituted, aryl group optionally substituted or arylcarbonyl group optionally substituted.

13. The process of claim 3 wherein the nucleonhilic agent (3) is a compound of a following formula (7):

R—OH wherein R is hydrogen atom, straight or branched alkyl group, straight or branched alkylcarbonyl group, aralkyl group optionally substituted, aralkylcarbonyl group optionally substituted, aryl group optionally substituted or arylcarbonyl group optionally substituted.

14. The process of claim 4 wherein the nucleonhilic agent (3) is a compound of a following formula (7):

R—OH wherein R is hydrogen atom, straight or branched alkyl group, straight or branched alkylcarbonyl group, aralkyl group optionally substituted, aralkylcarbonyl group optionally substituted, aryl group optionally substituted or arylcarbonyl group optionally substituted.

15. The process of claim 2 wherein M in the compound (2) is vanadium ion, chromium ion, manganese ion, iron ion, cobalt ion, nickel ion, molybdenum ion, ruthenium ion or tungsten ion.

16. The process of claim 3 wherein M in the compound (2) is vanadium ion, chromium ion, manganese ion, iron ion, cobalt ion, nickel ion, molybdenum ion, ruthenium ion or tungsten ion.

17. The process of claim 4 wherein M in the compound (6) is vanadium ion, chromium ion, manganese ion, iron ion, cobalt ion, nickel ion, molybdenum ion, ruthenium ion or tungsten ion.

18. The process of claim 5 wherein M in the compound (2) is vanadium ion, chromium ion, manganese ion, iron ion, cobalt ion, nickel ion, molybdenum ion, ruthenium ion or tungsten ion.

19. The process of claim 2 wherein A in the compound (2) is acetate, n-butyrate, (±)-comphorsulfonate, methanesulfonate, p-toluenesulfonate or trifluoromethanesulfonate.

20. The process of claim 3 wherein A in the compound (2) is acetate, n-butyrate, (±)-comphorsulfonate, methanesulfonate, p-toluenesulfonate or trifluoromethanesulfonate.

21. The process of claim 4 wherein A in the compound (6) is acetate, n-butyrate, (±)-comphorsulfonate, methanesulfonate, p-toluenesulfonate or trifluoromethanesulfonate.

22. The process of claim 5 wherein A in the compound (2) is acetate, n-butyrate, (±)-comphorsulfonate, methanesulfonate, p-toluenesulfonate or trifluoromethanesulfonate.

23. The process of claim 6 wherein A in the compound (2) is acetate, n-butyrate, (±)-comphorsulfonate, methanesulfonate, p-toluenesulfonate or trifluoromethanesulfonate.

24. The process of claim 2 wherein the process for preparation for the compound (4) starting from the compound (1) is carried out in an ether as a reaction solvent.

25. The process of claim 3 wherein the process for preparation for the compound (4) starting from the compound (1) is carried out in an ether as a reaction solvent.

26. The process of claim 4 wherein the process for preparation for the compound (4) starting from the compound (1) is carried out in an ether as a reaction solvent.

27. The process of claim 5 wherein the process for preparation for the compound (4) starting from the compound (1) is carried out in an ether as a reaction solvent.

28. The process of claim 6 wherein the process for preparation for the compound (4) starting from the compound (1) is carried out in an ether as a reaction solvent.

29. The process of claim 7 wherein the process for preparation for the compound (4) starting from the compound (1) is carried out in an ether as a reaction solvent.

\* \* \* \* \*